(12) United States Patent
Ford et al.

(10) Patent No.: US 9,440,917 B2
(45) Date of Patent: Sep. 13, 2016

(54) METHOD FOR PRODUCING 4-HALOALKYL-3-MERCAPTO-SUBSTITUTED 2-HYDROXY-BENZOIC ACID DERIVATIVES

(71) Applicant: BAYER CROPSCIENCE AG, Monheim (DE)

(72) Inventors: Mark James Ford, Schmitten (DE); Gunter Karig, Frankfurt am Main-Hoechst (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/650,905

(22) PCT Filed: Dec. 10, 2013

(86) PCT No.: PCT/EP2013/076014
§ 371 (c)(1),
(2) Date: Jun. 10, 2015

(87) PCT Pub. No.: WO2014/090766
PCT Pub. Date: Jun. 19, 2014

(65) Prior Publication Data
US 2015/0322003 A1    Nov. 12, 2015

(30) Foreign Application Priority Data
Dec. 14, 2012   (EP) .................. 12197102

(51) Int. Cl.
*C07C 321/00*   (2006.01)
*C07C 319/20*   (2006.01)
*C07C 323/54*   (2006.01)

(52) U.S. Cl.
CPC ........... *C07C 319/20* (2013.01); *C07C 323/54* (2013.01)

(58) Field of Classification Search
CPC .. C07C 319/20; C07C 323/62; C07C 323/54
See application file for complete search history.

(56) References Cited

U.S. PATENT DOCUMENTS

2011/0045980 A1   2/2011   Ahrens et al.
2011/0053779 A1   3/2011   Ahrens et al.

OTHER PUBLICATIONS

Rashid et al. Regioselective synthesis of diaryl sulfides by [3+3] cyclizations of 1,3-bis(trimethylsilyloxy)-1,3-dienes, Tetrahedron Letters 48 (2007) 2321-2323.*
International Search Report from corresponding PCT/EP2013/076014, mailed May 13, 2014.
M.A. Rashid et al., "Regioselective synthesis of diaryl sulfides by [3+3] cyclisations of 1,3-bis(trimethylsilyloxy)-1,3-dienes", Tetrahedron Letters, Elsevier Science Publishers, Amsterdam, NL, Bd. 48, Nr. 13, Feb. 1, 2007, XP005908501.

* cited by examiner

*Primary Examiner* — Yevegeny Valenrod
*Assistant Examiner* — Blaine G Doletski
(74) *Attorney, Agent, or Firm* — McBee Moore Woodward Vanik IP, LLC

(57) ABSTRACT

A process is described for preparing 4-haloalkyl-3-mercapto-substituted 2-hydroxybenzoic acid derivatives of the general formula (I) by reaction of 4-thio-substituted β-keto esters of the formula (II) with alkoxyvinyl haloalkyl ketones of the formula (III) in the presence of a base.

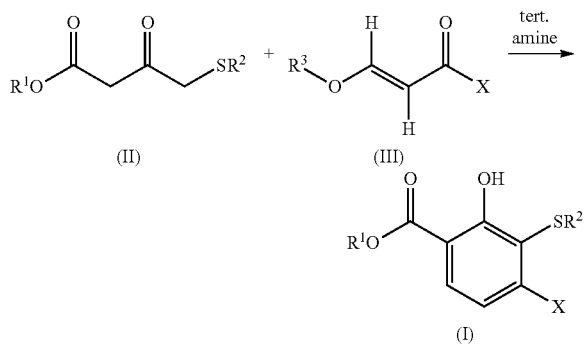

In the above formulae, X, $R^1$, $R^2$ and $R^3$ are each hydrogen, halogen, alkyl, alkoxy and cycloalkyl.

11 Claims, No Drawings

METHOD FOR PRODUCING 4-HALOALKYL-3-MERCAPTO-SUBSTITUTED 2-HYDROXY-BENZOIC ACID DERIVATIVES

CROSS REFERENCE TO RELATED APPLICATIONS

This application is a §371 National Stage Application of PCT/EP2013/076014, filed 10 Dec. 2013, which claims priority to EP 12197102.2, filed 14 Dec. 2012.

BACKGROUND

1. Field of the Invention

The invention relates to processes for preparing 4-haloalkyl-3-mercapto-substituted 2-hydroxybenzoic acid derivatives and to the use thereof as intermediates for the synthesis of fine chemicals and of active agrochemical ingredients.

2. Description of Related Art

4-Haloalkyl-3-mercapto-substituted 2-hydroxybenzoic acid derivatives of the formula (I) constitute an important structural element in a multitude of agronomically active substances, as disclosed, for example, in US 2011/0045980 A1 and US 2011/0053779 A1.

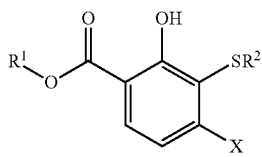

However, the processes specified in these documents for preparing 4-haloalkyl-3-mercapto-substituted 2-hydroxybenzoic acid derivatives are restricted to performance on the laboratory scale, since they have a number of disadvantages and are thus unusable for industrial production: costly starting materials, multitude of reaction steps, reactions at very low temperatures.

SUMMARY

It is an object of the present invention to provide a process for preparing 4-haloalkyl-3-mercapto-substituted 2-hydroxybenzoic acid derivatives, which overcomes the disadvantages of the processes known from the prior art.

It has now been found that 4-haloalkyl-3-mercapto-substituted 2-hydroxybenzoic acid derivatives can be prepared inexpensively and in high yields by reaction of 4-thio-substituted β-keto esters with alkoxyvinyl haloalkyl ketones at a temperature of ≥−30° C. in the presence of a base and of a solvent.

The present invention thus provides a process for preparing 4-haloalkyl-3-mercapto-substituted 2-hydroxybenzoic acid derivatives of the general formula (I), characterized in that 4-thio-substituted β-keto esters of the formula (II) are reacted with alkoxyvinyl haloalkyl ketones of the formula (III) at a temperature of ≥−30° C. in the presence of a tertiary amine and of a solvent, and in which the radicals, symbols and indices are each defined as follows:

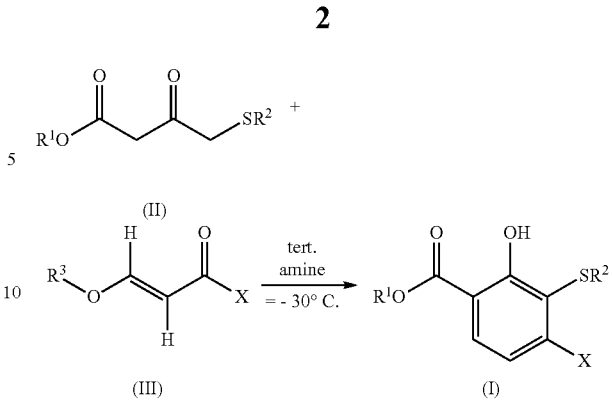

$R^1$, $R^2$ and $R^3$ are each independently ($C_1$-$C_6$)-alkyl substituted by p radicals from the group consisting of fluorine, chlorine, ($C_1$-$C_4$)-alkoxy and ($C_3$-$C_7$)-cycloalkyl, ($C_3$-$C_7$)-cycloalkyl substituted by p radicals from the group consisting of fluorine, chlorine, ($C_1$-$C_4$)-alkyl, ($C_1$-$C_4$)-alkoxy and ($C_3$-$C_7$)-cycloalkyl, phenyl, 1-naphthyl, 2-naphthyl or 5- or 6-membered heteroaryl, each substituted by p radicals from the group consisting of fluorine, chlorine, bromine, iodine, ($C_1$-$C_4$)-alkyl, ($C_1$-$C_4$)-alkoxy, ($C_3$-$C_7$)-cycloalkyl and ($C_1$-$C_4$)-alkylthio, where said heteroaryl contains one or two heteroatoms from the group consisting of oxygen and nitrogen, X is halo-($C_1$-$C_4$)-alkyl, p is 0, 1, 2, 3 or 4.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. ($C_3$-$C_7$)-Cycloalkyl represents cyclopropyl, cyclobutyl, cyclopentyl, cyclohexyl and cycloheptyl.

Halogen is fluorine, chlorine, bromine or iodine, preferably fluorine or chlorine.

Heteroaryl represents, for example, furanyl, imidazolyl, isoxazolyl, isothiazolyl, oxazolyl, pyrazinyl, pyrimidinyl, pyridazinyl, pyridinyl, pyrrolyl and pyrazolyl.

When a group is polysubstituted by radicals, this means that this group is substituted by one or more identical or different radicals from those mentioned.

In the process according to the invention, the radicals, symbols and indices are preferably each defined as follows:

$R^1$, $R^2$ and $R^3$ are each independently ($C_1$-$C_4$)-alkyl substituted by p radicals from the group consisting of fluorine, chlorine, ($C_1$-$C_2$)-alkoxy and ($C_3$-$C_7$)-cycloalkyl, ($C_3$-$C_7$)-cycloalkyl substituted by p radicals from the group consisting of fluorine, chlorine, ($C_1$-$C_2$)-alkyl and ($C_1$-$C_2$)-alkoxy, phenyl substituted by p radicals from the group consisting of fluorine, chlorine, bromine, iodine, ($C_1$-$C_2$)-alkyl, ($C_1$-$C_2$)-alkoxy, ($C_3$-$C_7$)-cycloalkyl and ($C_1$-$C_2$)-alkylthio, X is fluoro-($C_1$-$C_3$)-alkyl or chloro-($C_1$-$C_3$)-alkyl, p is 0, 1, 2, 3 or 4.

In a particularly preferred embodiment, X is $CF_3$, $CF_2H$, $CFH_2$, $CFClH$, $CF_2CH_3$, $CF(CH_3)_2$, $CF_2CF_3$ or $CH_2CF_3$.

The compounds of the formulae (II) and (III) are typically used in equimolar amounts. Suitable tertiary amines are, for example, trialkylamines such as triethylamine, tributylamine, diisopropylethylamine, diethylbenzylamine or dimethylbenzylamine; substituted or unsubstituted N-alkylpiperidines, N-alkylmorpholines or N-alkylpyrrolidines. The tertiary amine is used either as a single compound or as a mixture of two or more amines, in a catalytic or equimolar amount or in excess (0.05 to 5 equivalents, preferably 0.1 to 3 equivalents, more preferably 0.5 to 1.5 equivalents), based on the compounds of the formulae (II) and (III).

Suitable solvents are aprotic solvents such as ethers (preferably tetrahydrofuran), nitriles (preferably acetonitrile and butyronitrile), haloalkanes (preferably dichloromethane), esters (preferably ethyl acetate, butyl acetate and isopropyl acetate) and aromatics (preferably toluene, xylene, chlorobenzene, benzonitrile, anisole and benzotrifluoride), and mixtures of these said solvents. Particular preference is given to acetonitrile.

The preparation of the 4-thio-substituted β-keto esters of the formula (II) is described, for example, in WO 2010/59241 A1 and U.S. Pat. No. 4,521,613.

The preparation of the alkoxyvinyl haloalkyl ketones of the formula (III) is described, for example, in US 2008/269059 A1.

The process according to the invention is generally performed by initially charging the compounds of the formulae (II) and (III) in an organic solvent and adding the amine dropwise while cooling. The process according to the invention can also be performed by initially charging the compound of the formula (II) and the amine in an organic solvent and adding the compound of the formula (III) dropwise while cooling. The latter variant is preferable.

Typically, the process according to the invention is performed between −30° C. and 50° C., preferably within the range from −10° C. to 30° C.

The process according to the invention is typically performed under ambient pressure or under pressure up to 2 bar. It is preferably performed under ambient pressure.

The compounds of the formula (II) can also be used in the process according to the invention in the form of salts, such as sodium or potassium salts.

Typically, after addition of all the co-reactants, the mixture is left to stir for up to another 96 hours, preferably 0.05 to 24 hours.

It may be advantageous to purify the reaction mixture after the reaction has ended by treatment with aqueous base, for example sodium hydroxide solution or potassium hydroxide solution.

In that case, the compound of the formula (I) is worked up and isolated by customary methods known to those skilled in the art.

In the context of the present invention, it has been found that the compounds of the formulae (II) and (III) first react to give addition products of the formula (Ia), which are present with their tautomers in an equilibrium, and then react further to give the compounds of the formula (I).

The addition products of the formula (Ia) are novel and likewise form part of the subject-matter of the present invention.

If the compounds of the formula (II) are used in the form of their salts, the compounds of the formula (Ia) are accordingly also present in the form of their salts.

The examples which follow illustrate the process according to the invention in detail.

1. Preparation of 4-trifluoromethyl-3-methylthio-2-hydroxybenzoic acid ethyl ester 100 g of ethyl 4-(methylsulphanyl)-3-oxobutanoate and 27.8 g of triethylamine were initially charged in 260 ml of toluene and cooled to 0° C. under nitrogen. Then 102.8 g of 4-ethoxy-1,1,1-trifluorobut-3-en-2-one were added dropwise at 0-7° C. within 30 minutes and the mixture was stirred for a further 5 h. After 16 hours, the reaction was warmed up to 18° C. The reaction mixture was concentrated, admixed with 150 ml of acetonitrile and concentrated at 5 mbar. The crude product was admixed with 2 equivalents of 10% sodium hydroxide solution while stirring and cooling with ice-water and stirred for 1 h, and the solids were filtered off with suction, washed three times with 50 ml of 3.5% sodium hydroxide solution and dried by suction. The solids were then admixed with 150 ml of water and 150 ml of toluene, and adjusted to pH 1 with about 150 ml of 10% HCl, and further HCl was metered in with continued stirring until the pH remains below 3. Then the filtered phases were separated and the water phase was extracted once more with toluene. The combined toluene phases were dried and concentrated: Yield 122.3 g (78% of theory). $^1$H NMR (CDCl$_3$, 400 MHz): δ=11.77 ppm (1H, s), 7.93 ppm (1H, d), 7.23 ppm (1H, d), 4.47 ppm (2H, q), 2.44 ppm (3H, s), 1.45 ppm (3H, t).

2. Preparation of 4-difluoromethyl-3-methylthio-2-hydroxybenzoic acid ethyl ester 60 g of ethyl 4-(methylsulphanyl)-3-oxobutanoate and 61.3 g of 4-ethoxy-1,1,1-trifluorobut-3-en-2-one were initially charged in 312 g of acetonitrile and cooled to 0° C. under nitrogen. Within 30 minutes, 17.2 g of triethylamine were added dropwise at 0° C. and then stirring of the mixture at 0° C. continued for 2 hours. The reaction was stirred at 20° C. overnight, concentrated and admixed with 265 g of 10% sodium hydroxide solution, the mixture was stirred for 1 h, and the solids were filtered off with suction, washed 3 times with 50 ml of 3.5% NaOH and dried by suction. The solids were then admixed with 250 ml of water and 250 ml of toluene, and adjusted to pH 1 with 10% HCl, and further HCl was metered in with continued stirring until the pH remains below 3. Finally, the filtered phases were separated and the water phase was extracted once more with toluene. The combined toluene phases were dried and concentrated: Yield 53.7 g (60.1% of theory). $^1$H NMR (CDCl$_3$, 400 MHz): δ=11.73 ppm (1H, s), 7.95 ppm (1H, d), 7.22 ppm (1H, d), 7.11-7.25-7.39 ppm (1H, t, CHF2), 4.46 ppm (2H, q), 2.41 ppm (3H, s), 1.44 ppm (3H, t).

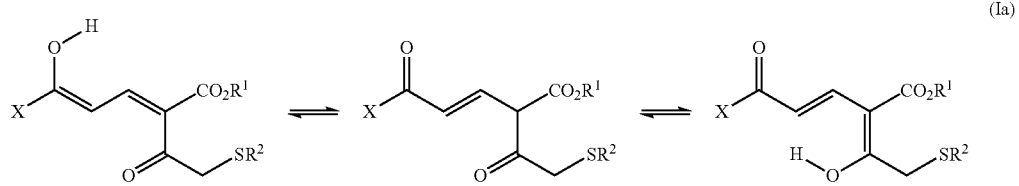

(Ia)

3. Preparation of 4-(chlorodifluoromethyl)-3-methylthio-2-hydroxybenzoic acid ethyl ester 1.1 g of ethyl 4-(methylsulphanyl)-3-oxobutanoate and 0.294 g of triethylamine in 3.3 ml of toluene were initially charged under argon and cooled to 0° C. Within 15 minutes at 0-7° C., 1.385 g of 4-ethoxy-1,1,1-trifluorobut-3-en-2-one were added dropwise. The reaction was warmed up to 20° C. and stirred overnight. The solvent was concentrated and the residue was admixed with 4.64 g of NaOH (10% strength) while cooling with ice, and stirred for 6 h. The precipitate was filtered off with suction using a POR3 glass frit, and washed with a little ice-water and then with n-heptane. 10% HCl was added to the still-moist solid, and the mixture was blanketed with toluene and stirred (2 h) until two clear layers had formed. The phases were separated and the water phase was extracted once with toluene. The combined organic phases were dried and concentrated. Yield 1.25 g (70.5% of theory). $^1$H NMR (CDCl$_3$, 400 MHz): δ=11.79 (1H, s), 7.91 (1H, d), 7.20 (d, 1H), 4.47 (2H, q), 2.45 (3H, s), 1.44 ppm (3H, t).

4. Preparation of 4-(chlorodifluoromethyl)-3-(4-fluorophenylthio)-2-hydroxybenzoic acid ethyl ester In analogy to the above Example 3, 4-(chlorodifluoromethyl)-3-(4-fluorophenylthio)-2-hydroxybenzoic acid ethyl ester was prepared in 57.6% yield (of theory). $^1$H NMR (CDCl$_3$, 400 MHz): δ=11.64 ppm (1H, s), 8.01 ppm (1H, d), 7.32 ppm (1H, d), 7.23-7.28 ppm (2H, m), 6.90-6.99 ppm (2H, m), 4.44 ppm (2H, q), 1.43 ppm (3H, t).

The invention claimed is:

1. Process for preparing 4-haloalkyl-3-mercapto-substituted 2-hydroxybenzoic acid derivative of formula (I), comprising reacting 4-thio-substituted β-keto ester of formula (II) with alkoxyvinyl haloalkyl ketone of formula (III) at a temperature of ≥−30° C. in the presence of a tertiary amine and of a solvent, and in which the radicals, symbols and indices are each defined as follows:

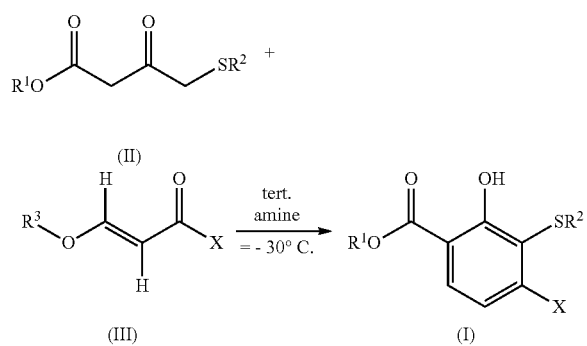

$R^1$, $R^2$ and $R^3$ are each independently ($C_1$-$C_6$)-alkyl substituted by p radicals from the group consisting of fluorine, chlorine, ($C_1$-$C_4$)-alkoxy and ($C_3$-$C_7$)-cycloalkyl, ($C_3$-$C_7$)-cycloalkyl substituted by p radicals from the group consisting of fluorine, chlorine, ($C_1$-$C_4$)-alkyl, ($C_1$-$C_4$)-alkoxy and ($C_3$-$C_7$)-cycloalkyl, phenyl, 1-naphthyl, 2-naphthyl or 5- or 6-membered heteroaryl, each substituted by p radicals from the group consisting of fluorine, chlorine, bromine, iodine, ($C_1$-$C_4$)-alkyl, ($C_1$-$C_4$)-alkoxy, ($C_3$-$C_7$)-cycloalkyl and ($C_1$-$C_4$)-alkylthio, where said heteroaryl contains one or two heteroatoms from the group consisting of oxygen and nitrogen, X is halo-($C_1$-$C_4$)-alkyl, p is 0, 1, 2, 3 or 4.

2. Process according to claim 1, in which the radicals, symbols and indices are each defined as follows:

$R^1$, $R^2$ and $R^3$ are each independently ($C_1$-$C_4$)-alkyl substituted by p radicals from the group consisting of fluorine, chlorine, ($C_1$-$C_2$)-alkoxy and ($C_3$-$C_7$)-cycloalkyl, ($C_3$-$C_7$)-cycloalkyl substituted by p radicals from the group consisting of fluorine, chlorine, ($C_1$-$C_2$)-alkyl and ($C_1$-$C_2$)-alkoxy, phenyl substituted by p radicals from the group consisting of fluorine, chlorine, bromine, iodine, ($C_1$-$C_2$)-alkyl, ($C_1$-$C_2$)-alkoxy, ($C_3$-$C_7$)-cycloalkyl and ($C_1$-$C_2$)-alkylthio, X is fluoro-($C_1$-$C_3$)-alkyl or chloro-($C_1$-$C_3$)-alkyl, p is 0, 1, 2, 3 or 4.

3. Process according to claim 1, in which X is $CF_3$, $CF_2H$, $CFH_2$, $CFClH$, $CF_2CH_3$, $CF(CH_3)_2$, $CF_2CF_3$ or $CH_2CF_3$.

4. Process according to claim 1, wherein 0.1 to 3 equivalents of the tertiary amine are used.

5. Process according to claim 1, wherein 0.5 to 1.5 equivalents of the tertiary amine are used.

6. Process according to claim 1, wherein acetonitrile is used as the solvent.

7. Process according to claim 1, wherein the compound of formula (II) and the amine are initially charged in an organic solvent and the compound of formula (III) is added dropwise while cooling.

8. Process according to claim 1, wherein the reaction is performed at a temperature of −30° C. and 50° C.

9. Process according to claim 1, wherein the reaction is performed at a temperature of −10° C. to 30° C.

10. Process according to claim 1, wherein the reaction mixture is treated after reaction has ended with aqueous NaOH solution or KOH solution.

11. Compound of formula (Ia)

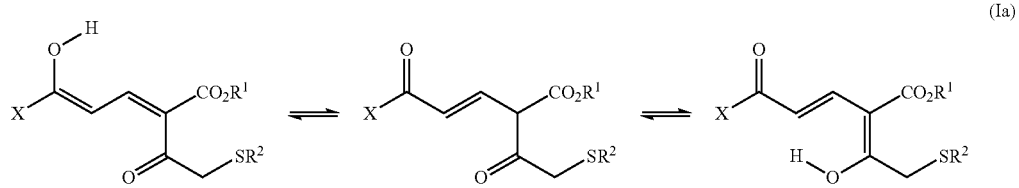

And/or a tautomer thereof, in which $R^1$, $R^2$ and $R^3$ are each independently $(C_1-C_6)$-alkyl substituted by p radicals from the group consisting of fluorine, chlorine, $(C_1-C_4)$-alkoxy and $(C_3-C_7)$-cycloalkyl, $(C_3-C_7)$-cycloalkyl substituted by p radicals from the group consisting of fluorine, chlorine, $(C_1-C_4)$-alkyl, $(C_1-C_4)$-alkoxy and $(C_3-C_7)$-cycloalkyl, phenyl, 1-naphthyl, 2-naphthyl or 5- or 6-membered heteroaryl, each substituted by p radicals from the group consisting of fluorine, chlorine, bromine, iodine, $(C_1-C_4)$-alkyl, $(C_1-C_4)$-alkoxy, $(C_3-C_7)$-cycloalkyl and $(C_1-C_4)$-alkylthio, where said heteroaryl contains one or two heteroatoms from the group consisting of oxygen and nitrogen, X is halo-$(C_1-C_4)$-alkyl, p is 0, 1, 2, 3 or 4.

* * * * *